United States Patent [19]
Winkowski et al.

[11] Patent Number: 6,121,198
[45] Date of Patent: Sep. 19, 2000

[54] SYNERGISTIC COMPOSITION OF BIOCIDES

[75] Inventors: Karen Winkowski, Highland Park, N.J.; Techen Tsao, Baton Rouge, La.

[73] Assignee: Creanova Inc., Somerset, N.J.

[21] Appl. No.: 09/317,752

[22] Filed: May 24, 1999

[51] Int. Cl.[7] .......................... A01N 33/00; A01N 37/34; A01N 47/10
[52] U.S. Cl. .......................... 504/157; 504/158; 514/478; 514/479; 514/525
[58] Field of Search .................... 504/158, 157; 514/525, 478, 479

[56] References Cited

U.S. PATENT DOCUMENTS

| | | | |
|---|---|---|---|
| 3,948,636 | 4/1976 | Marks | 71/112 |
| 4,260,753 | 4/1981 | Berrer et al. | 544/208 |
| 4,297,258 | 10/1981 | Long, Jr. | 260/29.6 |
| 5,125,953 | 6/1992 | Gattner et al. | 71/67 |
| 5,162,343 | 11/1992 | Whitekettle et al. | 514/345 |
| 5,328,926 | 7/1994 | Oppong | 514/372 |
| 5,401,757 | 3/1995 | Backhouse et al. | 514/347 |
| 5,585,033 | 12/1996 | Tsao et al. | 514/373 |
| 5,591,760 | 1/1997 | Hsu | 514/372 |
| 5,707,929 | 1/1998 | Kuusisto et al. | 504/155 |
| 5,716,628 | 2/1998 | Vinopal et al. | 424/405 |
| 5,716,629 | 2/1998 | Robertson et al. | 424/405 |
| 5,726,206 | 3/1998 | Oppong et al. | 514/544 |
| 5,728,730 | 3/1998 | Oppong et al. | 514/515 |
| 5,733,362 | 3/1998 | Hahn | 106/18.33 |
| 5,741,483 | 4/1998 | Okawa | 424/78.09 |
| 5,874,453 | 2/1999 | Oppong et al. | 514/367 |
| 5,877,201 | 3/1999 | Ammermann et al. | 514/417 |

FOREIGN PATENT DOCUMENTS 7900654  6/1979  WIPO .

OTHER PUBLICATIONS

Rainer Gruening, Ph.D., "IPBC Preservative Combination Systems for Material Protection", *Cosmetics and Toiletries Magazine*, vol. 112, Apr. 1997.

*Primary Examiner*—Allen J. Robinson
*Attorney, Agent, or Firm*—Abelman, Frayne & Schwab

[57] ABSTRACT

The invention is directed to a biocidal composition for inhibition fungal, bacterial and algae growth which comprises a mixture of tetrachloroisophthalonitrile and 3-iodo-2-propynly butyl carbamate.

8 Claims, No Drawings

SYNERGISTIC COMPOSITION OF BIOCIDES

FIELD OF THE INVENTION

This invention is directed to a biocidal composition containing tetrachloroisophthalonitrile and 3-iodo-2-propynylbutylcarbamate in the form of a liquid which serves to inhibit fungal, algae and bacterial growth.

DESCRIPTION OF RELATED ART

The compound 3-iodo-2-propynyl butylcarbamate (hereinafter referred to as "IPBC") is a well-known biocide, having good fungicidal activity. It also has activity against bacterial and unicellular green algae, but has been found to be much less effective against unicellular blue green algae.

IPBC has been mixed with various biocides in combination form for various applications. U.S. Pat. No. 5,162,343 discloses IPBC with sodium 2-pyridinethiol-1-oxide in a biocidal composition. U.S. Pat. No. 5,328,926 discloses IPBC with 1,2-Benzisothiazolin-3-one for use in controlling the growth of fungi and bacteria in fluids. U.S. Pat. No. 5,591,760 discloses IPBC with 4,5-dichloro-2-octyl-3-isothiazolone in various applications. U.S. Pat. No. 5,707,929 discloses IPBC with N-Cyclopropyl-N' (1,1-dimethyl)-6-(methylthio)-1,3,5-triazine-2,4-dismine as a fungicide and algaecide.

Tetrachloroisophthalonitrile (hereinafter referred to as "CTL") has been used as a fungicide in agriculture and in architectural coating applications i.e., paints, stains, and other related coatings. It provides very good, long-term fungicidal protection in the cured coating.

U.S. Pat. No. 3,948,636 discloses the formulation of tetrachloroisophthalonitrile as a flowing aqueous dispersion. PCT WO 79/00654 discloses tetrachloroisophthalonitrile in surfactants and non-aqueous media for coating applications. U.S. Pat. No. 5,401,757 discloses tetrachloroisophthalonitrile in biocidal compositions with substituted urea and sulfoxide or sulfone.

Although the principal utility disclosed for CTL has been as a fungicide, this compound exhibits activity against gram-positive bacteria and unicellular blue green algae (Cyanophyceae family, such as Oscillatoria sp., Scytonema sp., Gloeocapsa sp., Chroococcus sp., Calothrix sp., etc.). Those species are very commonly found on substrates to be covered with exterior paints, in sea water environments, and on various coatings, and cannot be inhibited by IPBC.

SUMMARY OF THE INVENTION

In accordance with the present invention, it has now surprisingly been found that when IPBC and CTL are employed in combination in the form of a liquid dispersion, they constitute a broad-spectrum biocidal composition displaying bactericidal, fungicidal and algaecidal activity. The composition is easy to use and is an environmentally friendly mixture suitable for use in both water-based and solvent-based applications.

The combination of IPBC and CTL provides both short-term and long-term protection for coatings, as well as protection against bacteria, fungi and algae, when employed in coating applications.

Further, as will be seen from the examples which follow, the combination of IPBC and CTL produce biocidal results in combination which is greater than the sum of the biocidal results that are produced when each is used separately. In other words, a synergistic result is obtained.

DETAILED DESCRIPTION OF THE INVENTION

The present invention is directed to a biocidal composition suitable for controlling unwanted bacterial, fungal, and algae growth in water-based and solvent-based applications. The liquid biocidal compositions of the present invention comprise a synergistic mixture of CTL and IPBC. The weight ratio of CTL to IPBC in the present invention preferably ranges from about 0.01:99 to about 99:0.01, more preferably from about 1:10 to about 10:1, and most preferably from about 1:4 to about 4:1. The composition can also contain from about 0% to about 40% by weight of one or more surfactants, exemplary of which are EO IPO block copolymers, such as Witcomol®324, sulfosuccinates, naphthalene sulfonates, and acrylic graft copolymers, which serve the combined function of a wetting agent, dispersant, emulsifier, and defoamer for both the CTL and IPBC.

The composition also contains from about 0% to about 50%, by weight, of an environmentally friendly organic solvent for the purpose of functioning as a co-solvent to stabilize the dispersion which is formed. Exemplary of the solvents which can be employed are propylene glycol methyl ether, dipropylene glycol methyl ether, tripropyleneglycol methyl ether, propylene glycol methyl ether acetate, propylene glycol phenyl ether, propylene glycol propyl ether, propylene glycol butyl ether, and other common solvents which are known of or used in coating applications.

The composition can also contain from 0% to about 5% of fused silica, a modified or unmodified carbohydrate polymer, a polyurethane or an acrylic type material to function as a thickener or anti-settling agent by which the viscosity is established and maintained over time and also to avoid the settling of solids with the passage of time.

The composition of the present invention has utility for retarding microbial growth, including bacterial, fungal and algae growth, in paints, marine anti-fouling coatings, cooling towers, metal working fluids, fuel systems, swimming pools, coatings, fabric, leather, paper, wood, cosmetic formulations and other personal care products, therapeutic pharmaceutical formulations, and the like.

The examples presented below serve to illustrate the invention and to demonstrate the synergistic results obtained when CTL and IPBC are used in combination as compared with their effectiveness when used individually.

The bacterial, fungal and algae tests set forth below were conducted to demonstrate the synergism of the two-component compositions of the present invention by testing over a wide range of concentrations and ratios of CTL and IPBC. For the microorganisms listed in Tables I and II, three independent experimental determinations were done for each bacteria, two independent experimental determinations for each fungi and one experimental determination for each algae.

A. For bacterial evaluation TSA or TSB media from Sigma-Aldrich was used. The medium was autoclaved at 121° C. for 20 minutes prior to the addition of the biocides. After addition of the biocides in the indicated concentrations to the media, 100$\mu$l of a suspension of the testing bacteria (*Bacillus subtilis* ATCC 27328 or *Staphylococcus aureus* ATCC 6588) was added to a final concentration of approximately $10^6$ CFU/ml. The inoculated media was incubated at 32° C. for 5–7 days.

B. For fungal evaluations, a mineral salts-glucose was used as a liquid medium. Malt agar from Sigma-Aldrich was used as a solid medium. The mineral salts-glucose medium contained: 0.7 g of $KH_2PO_4$, 0.7 g of $MgSO_4.7H_2O$, 1.0 g of $NH_4NO_3$, 0.005 g NaCl, 0.002 g $FeSO_4.7H_2O$, 0.002 g $Z_nSO_4.7H_2O$, 0.001 g of glucose, dissolved in 1.0 liter of deionized water. The pH of the medium was adjusted to 6 with 1N NaOH. Both media were autoclaved at 121° C. for 20 minutes prior to the addition of biocides. Each fungi (*Aspergillus niger* ATCC 6275, *A. orizae* ATCC 10191, *Aureobasidium pullulans* ATCC 9348 or *Gliocladium virens* ATCC 9645), was grown on Malt agar for 10 days and a spore suspension was prepared by washing the spores from the plate into a sterile water solution. After the addition of the biocides in the indicated concentrations to the medium, the fungal spore suspension was added. The final spore concentration was approximately $10^6$ spores/ml. The inoculated media was incubated at 28° C. for 7–10 days.

C. For algae evaluations, modified Allen's medium was used. To prepare the medium, the following ingredients were added to 1.0 liter of deionized water: 1.5 g of $NaNO_3$, 0.039 g of $K_2HPO_4$, 0.075 g of $MgSO_4.7H_2O$, 0.027 g of $CaCl_2.2H_2O$, 0.02 g of $Na_2CO_3$, 0.058 g of $Na_2SiO_3.9H_2O$, 0.006 g of Ferric Citrate (autoclaved separately and added after cooling), 0.006 g of citric acid, 0.001 g of EDTA and 1.0 ml of Allen's trace-element. The trace-element solution was prepared by adding to 1.0 liter of deionized water: 2.86 g of $H_3BO_3$, 1.81 g of $MnCl_2.4H_2O$, 0.222 g of $ZnSO_4.7H_2O$, 0.391 g of $Na_2MoO_4.2H_2O$, 0.079 g of $CuSO_4.5H_2O$ and 0.0494 g of $Co(NO_3)_2.6H_2O$. The pH of the medium was adjusted to 7.8 with 1 N NaOH. For solid media, 1.5% of bacto agar (Sigma-Aldrich) was added. The medium was autoclaved at 121° C. for 20 minutes prior to the addition of the biocides. Each algae (*Chlorella* sp. ATCC 7516, *Calothirx* sp. ATCC 27914 or *Gloeocapsa* sp. ATCC 29115) was grown on 3N Bold's Basal Medium for 10 days and the cell suspension prepared by washing the cells from the plate into a sterile water solution. After the addition of the biocides in the indicated concentration to the medium, the algae suspension was added to a final concentration of $10^6$ cells/ml. The inoculated media was incubated at 25° C. for 10–15 days under a light-dark cycle of 14–10 hours.

The lowest concentration of each compound or mixture of compounds sufficient to inhibit visible growth was taken as the minimum inhibitory concentration (MIC). The MIC were taken as end points of activity. End points for the mixture of CTL and IPBC were then compared with the end points for the pure active compound when employed individually.

Synergism was determined by a commonly used and accepted method described by Kull A. C,; Eisman, P. C.; Sylwestrowicz, H. D. and Mayer, R. L. 1961. *Applied Microbiology*, 9:538–541 using the ratio determined by:

Qa/QA+Qb/QB=Synergy Index wherein:

QA is the concentration of compound CTL in parts per million (PPM), acting alone, which produced an end point.

Qa is the concentration of compound CTL in PPM, in the mixture, which produced an end point.

QB is the concentration of compound IPBC in PPM, acting alone, which produced an end point.

Qb is the concentration of compound IPBC in PPM, in the mixture, which produced an end point.

When the sum of Qa/QA+Qb/QB is greater than one, antagonism is indicated.

When the sum is equal to one, additivity is indicated.

When the sum is less than one, synergism is demonstrated.

The results which serve to demonstrate the synergism of this biocidal combination are compiled in Tables I and II below. Each of the tables demonstrates mixtures of CTL and IPBC in various concentrations and ratios which shows:

1. Test Organism (Bacteria, Fungi, and Algae).
2. The end-point activity in PPM measured by MIC for the compound A alone (QA), for compound A in the mixture (Qa), for compound B alone (QB), for compound B in the mixture (Qb).
3. The weight ratio of compound A to Compound B in that particular combination and the Synergy Index (SI) based on the formula SI=Qa/QA+Qb/QB.

TABLE I

Combination of CTL with IPBC (Solid Media)

| Microorganism | CTL(A) (PPM) | CTL(a) (PPM) | IPBC(B) (PPM) | IPBC(b) (PPM) | Ratio A:B | SI |
|---|---|---|---|---|---|---|
| Bacteria: | | | | | | |
| *B. subtilis* | 50 | 0.25 | 250 | 0.25 | 1:1 | 0.002 |
| | 50 | 16.6 | 250 | 8.3 | 2:1 | 0.36 |
| | 50 | 1.7 | 250 | 3.3 | 1:2 | 0.047 |
| *S. aureus* | 25 | 0.25 | 100 | 0.25 | 1:1 | 0.012 |
| | 25 | 16.6 | 100 | 8.33 | 2:1 | 0.74 |
| | 25 | 16.6 | 100 | 33.3 | 1:2 | 0.99 |
| Fungi: | | | | | | |
| *A. niger* | 5.0 | 0.25 | 0.5 | 0.25 | 1:1 | 0.55 |
| | 5.0 | 0.33 | 0.5 | 0.17 | 2:1 | 0.40 |
| | 5.0 | 0.17 | 0.5 | 0.33 | 1:2 | 0.69 |
| *A. orizae* | 1.0 | 0.5 | 1.0 | 0.5 | 1:1 | |
| | 1.0 | 0.33 | 1.0 | 0.17 | 2:1 | 0.50 |
| | 1.0 | 0.17 | 1.0 | 0.33 | 1:2 | 0.50 |
| *A. pullulans* | 100 | 2.5 | 2.0 | 2.5 | 1:1 | |
| | 100 | 3.33 | 2.0 | 1.67 | 2:1 | 0.87 |
| | 100 | 1.67 | 2.0 | 3.33 | 1:2 | |
| *G. virens* | 10.0 | 0.25 | 1.0 | 0.25 | 1:1 | 0.28 |
| | 10.0 | 0.66 | 1.0 | 0.33 | 2:1 | 0.40 |
| | 10.0 | 0.33 | 1.0 | 0.66 | 1:2 | 0.69 |
| Algae: | | | | | | |
| *Calothrix sp.* | 2.5 | 1.25 | 25 | 1.25 | 1:1 | 0.55 |
| | 2.5 | 1.67 | 25 | 0.83 | 2:1 | 0.70 |
| | 2.5 | 0.83 | 25 | 1.67 | 1:2 | 0.40 |
| *Gloeocapsa sp.* | 2.5 | 5 | 25 | 5 | 1:1 | |
| | 2.5 | 1.67 | 25 | 0.83 | 2:1 | 0.70 |
| | 2.5 | 3.33 | 25 | 1.67 | 1:2 | |

TABLE II

Combination of CTL with IPBC (Liquid Media)

| Microorganism | CTL(A) (PPM) | CTL(a) (PPM) | IPBC(B) (PPM) | IPBC(b) (PPM) | Ratio A:B | SI |
|---|---|---|---|---|---|---|
| Bacteria: | | | | | | |
| *B. subtilis* | 1.95 | 0.625 | 125 | 62.5 | 1:100 | 0.82 |
| Fungi: | | | | | | |
| *A. niger* | 2.5 | 1.25 | 250 | 250 | 1:200 | |
| Algae: | | | | | | |
| *Chlorella sp.* | 100 | 0.78 | 25 | 6.25 | 8:1 | 0.26 |

As can be seen from the data presented in Tables I and II, the compositions of the invention demonstrated synergistic microbiocidal activity against bacteria, fungi and algae. Thus, the combination of the two biocides not only lowers the use-level of the biocide but broadens the spectrum of activity. This is especially useful in situations where either biocide component alone does not achieve the best results due to weak activity against certain organisms.

What is claimed is:

1. A biocidal composition to control the growth of a microorganism selected from the group consisting of bacteria, fungi, and algae comprising a synergistically microbiocidally effective mixture consisting of tetrachloroisophthalonitrile (CTL) and 3-iodo-2-propynyl butyl carbamate (IPBC).

2. The composition of claim 1, wherein the weight ratio of CTL to IPBC is from about 0.01:99 to about 99:0.01.

3. The composition of claim 2, wherein the weight ratio of CTL to IPBC is from about 1:10 to about 10:1.

4. The composition of claim 3, wherein the weight ratio of CTL to IPBC is from about 1:4 to about 4:1.

5. A method of controlling the growth of bacteria, fungi and algae in an aqueous or solvent based formulation, which comprises adding to said aqueous formulation a bactericidal, fungicidal and algaecidal effective amount of a synergistic mixture, consisting of 3-iodo-2-propynyl butyl carbamate (IPBC) and tetrachloroisophthalonitrile (CTL).

6. The method of claim 5, wherein the weight ratio of CTL to IPBC is from about 0.01:99 to about 99:0.01.

7. The method of claim 6, wherein the weight ratio of CTL to IPBC is from about 1:10 to about 10:1.

8. The method of claim 7, wherein the weight ratio of CTL to IPBC is from about 1:4 to about 4:1.

* * * * *